United States Patent [19]

Chang

[11] Patent Number: 5,449,760

[45] Date of Patent: Sep. 12, 1995

[54] MONOCLONAL ANTIBODIES THAT BIND TO SOLUBLE IGE BUT DO NOT BIND IGE ON IGE EXPRESSING B LYMPHOCYTES OR BASOPHILS

[75] Inventor: Tse-wen Chang, Houston, Tex.

[73] Assignee: Tanox Biosystems, Inc., Houston, Tex.

[21] Appl. No.: 320,294

[22] Filed: Mar. 6, 1989

Related U.S. Application Data

[63] Continuation-in-part of Ser. No. 291,068, Dec. 28, 1988, abandoned, which is a continuation-in-part of Ser. No. 226,421, Jul. 29, 1988, Pat. No. 5,422,258, which is a continuation-in-part of Ser. No. 140,036, Dec. 31, 1987, abandoned.

[51] Int. Cl.⁶ .......................... C07K 16/42; C12N 5/70
[52] U.S. Cl. ........................... 530/387.3; 530/388.25; 530/389.3; 435/240.27
[58] Field of Search ............ 530/387, 380, 389, 387.3, 530/388.25, 389.3; 435/240.24, 172.2, 70.21

[56] References Cited

PUBLICATIONS

Goding, "Monoclonal Antibodies: Principles and Practice" Academic Press, 1983, pp. 118–123.
Waldmann, Science 252: 1657–1667, 1991.
Morrison, Science 229: 1202–1207, 1985.
Hook et al. Fed Proc. 46:1346, 1987.

*Primary Examiner*—Paula K. Hutzell
*Attorney, Agent, or Firm*—Eric P. Mirabel; Giulio A. DeConti, Jr.

[57] ABSTRACT

Antibodies that bind soluble IgE but not IgE on the surface of B lymphocytes or basophils are described. The antibodies do not induce histamine release by basophils or mast cells.

5 Claims, No Drawings

MONOCLONAL ANTIBODIES THAT BIND TO SOLUBLE IGE BUT DO NOT BIND IGE ON IGE EXPRESSING B LYMPHOCYTES OR BASOPHILS

RELATED APPLICATIONS

This application is a continuation-in-part of U.S. Ser. No. 07/291,068, filed Dec. 28, 1988 (now abandoned), which is a continuation-in-part of U.S. Ser. No. 226,421, filed Jul. 29, 1988, U.S. Pat. No. 5,422,258 which is a continuation-in-part of U.S. Ser. No. 140,036 filed Dec. 31, 1987 (now abandoned).

BACKGROUND

Immunoglobulin E (IgE) mediates type-I hypersensitivity reactions responsible for human allergic diseases such as asthma, hay fever, and food and drug allergies. IgE circulates in the blood, and binds to high affinity IgE Fc specific receptors ($Fc_\epsilon R$-I) on the surface of mast cells and basophils. In an IgE-mediated response, multivalent allergen crosslinks $Fc_\epsilon R$-I bound IgE on mast cells and basophils, thereby aggregates the underlying receptors and triggers the release of histamine and other vasoactive pharmacological mediators.

The treatment of IgE-mediated diseases has involved various approaches including the avoidance of offending allergens, the pharmacological therapy of symptoms and repeated injection of allergen in hyposensitization regimens. Frick, O. L. 1982. "Immediate hypersentivitiy." In *Basic and Clinical Immunology*, eds. Stites, D. P., Stobo, J. D. and Wells, J. V., Lange Medical Publications, Los Altos, Calif., pg 250. Other therapeutic strategies include the blockage of high affinity IgE Fc receptors and the inhibition of binding onto mast cells and basophils.

Fragments and synthetic peptides of the IgE Fc region have been proposed as competitive inhibitors of IgE binding to the high affinity receptor. (Hamburger, R. N. 1975. "Peptide inhibition of Prausnitz-Kustner reaction." *Science* 117:314–322; Stanworth, D. R., Burt, D. S. 1986. "Anti-E chain antibodies as probes in the study of mast cell triggering." *Mol. Immunol.* 23:1231. However, presumably due to the much lower affinity of these peptides compared with whole IgE for the $Fc_\epsilon R$, such peptides have not proven effcacious in blocking IgE binding onto the receptor.

Alternative strategies have been proposed which involve the modulation or down-regulation of IgE synthesis. Experimentally, IgE synthesis can be suppressed with T cell-derived IgE binding factors (Ishizaka K. 1984. "Regulation of IgE synthesis." *Ann. Rev. Immunol.* 2:195; Massicot J. G., Ishizaka, K. 1986. "Workshop on measurement of in vitro IgE synthesis and regulation of IgE synthesis." *J. Allergy Clin. Immunol.* 77:544–552.) Direct blockage of interleukin 4 (IL4) binding to its receptor might reduce IL4-induced B cell isotype switching to IgE and thus reduce IgE synthesis.

In earlier patent applications, U.S. Ser. Nos. 07/291,068, filed Dec. 28, 1988 (now abandoned) and U.S. Pat. No. 5,091,313, filed Nov. 16, 1988, the discovery of unique epitopes on B cell bound IgE, and of monoclonal antibodies that bind to IgE on B cells but not basophils and the various applications of these monoclonal antibodies in the treatment of patients with allergic diseases were described. The pharmacologic mechanism of therapies based on those antibodies is to target and to lyse IgE-producing B cells to decrease the synthesis of IgE.

SUMMARY OF THE INVENTION

This invention pertains to IgE-specific antibodies which bind to soluble IgE, but do not bind to IgE on B lymphocytes or on basophils and which do not induce histamine release from basophils. The antibodies bind epitopes unique to soluble IgE.

DETAILED DESCRIPTION OF THE INVENTION

This invention is based, in part, upon the discovery of antigenic epitopes unique to soluble forms of IgE. The epitopes are present on soluble IgE, but they are absent from IgE bound to the surface of IgE-producing lymphocytes and they are absent from IgE bound to the surface of basophils. The antibodies of this invention are specific for the unique epitopes of soluble IgE. The antibodies do not bind IgE on the surface of IgE-producing B lymphocytes or on the surface of basophils, and they do not induce histamine release from basophils or mast cells.

In preferred embodiments, the antibodies of this invention are monoclonal. Chimeric or "near-human" antibodies are preferred. Chimeric antibodies comprise a variable or antigen binding (hypervariable or complementarity determining) regions derived from an animal (e.g., a mouse) antibody and the remaining regions derived from a human antibody. Methods for producing chimeric (e.g. murine/human) antibodies are described below. Chimeric antibodies can be produced in large quantities and they are less immunogenic in humans than nonhuman antibodies.

The monoclonal anti-IgE antibodies of this invention are produced by continuous (immortalized), stable, antibody-producing cell lines. The preferred antibody-producing cell lines are hybridoma cell lines and myeloma cell lines. In principle, however, the cell lines can be any cells which contain and are capable of expressing functionally rearranged genes which encode the antibody variable regions of the antibody light and heavy chains. Preferably, the cell line should have the capability to assemble the chains into functional antibodies or antibody fragments. Thus, lymphoid cells which naturally produce immunoglobulin are most often employed. In addition to those previously mentioned, examples of suitable lymphoid cells are viral or oncogenically transformed lymphoid cells.

Hybridoma cells which produce the anti-IgE antibodies of this invention can be made by the standard somatic cell hybridization technique of Kohler and Milstein, *Nature* 256:495 (1975) or similar procedures employing different fusing agents. Briefly, the procedure is as follows: the monoclonal anti-IgE antibodies are produced by immunizing an animal with human IgE, or peptidic segments of human IgE. The peptides can be synthesized and conjugated to a carrier protein, such as keyhole limpet hemocyanin, to be used as an immunogen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired anti-IgE antibody.

Hybridoma production in rodents, especially mouse, is a very well established procedure. Stable murine hybridomas provide an unlimited source of antibody of select characteristics. Murine antibodies, however, may have limited use in the treatment of humans because they are highly immunogenic and can themselves induce untoward allergic reactions in the recipient. In the preferred embodiment of this invention, the anti-IgE antibodies are produced in a rodent system and are converted into chimeric rodent/human antibodies by the established techniques described in detail below. As explained above, these "near human", chimeric antibodies are preferred for in vivo administration, especially where multiple doses are required.

For the production of the anti-IgE antibodies of this invention, human IgE for immunization can be purified from human serum. Alternatively, human IgE may be produced by culturing an IgE-producing cell line (for example, the cell line U266, ATCC number CRL8033). Human IgE can be purified by affinity chromatography. Mouse monoclonal antibodies specific for human IgE are conjugated to a suitable matrix (such as cyanogen bromide-activated Sepharose 4B) to provide an IgE-specific immunoadsorbent. The IgE preparation can be contacted with the immunoadsorbent which selectively adsorbs IgE. The adsorbed IgE can thereafter be eluted in substantially pure form from the immunoadsorbent.

In preferred embodiments, animals are immunized with a vigorous immunization protocol in order to produce a high frequency of lymphocytes producing IgE-specific antibodies. Spleen cells are obtained from the immunized animal and fused with an immortalizing cells, preferably myeloma cells which have lost the ability to secrete immunoglobulin. Many suitable myeloma cell lines are known in the art. An example is the murine myeloma NS-1. Fusion of the spleen cells and fusion partner can be carried out in the presence of polyethylene glycol according to established methods. Techniques of electrofusion may also be used. The resulting hybrid cells are clonally cultured and then screened for production of anti-IgE antibody.

Hybridomas producing antibodies which are reactive with soluble IgE but not with IgE-bearing B cells or with basophils and which do not induce histamine release can be selected as follows. Hybridomas are first screened for production of antibody reactive with human IgE. This can be done by an enzyme-linked immunosorbent assay (ELISA) employing purified human IgE adsorbed to a solid phase.

Hybridomas can be screened for secretion of antibodies which do not react with IgE-bearing lymphocytes. The preferred methods are to test whether the antibodies in supernatants can stain cells expressing IgE on their surface using flow cytometric analysis with live cells or with ELISA with fixed cells on a solid phase. The determination can be first performed with IgE-producing myeloma SK007. As they are developed, IgE-specific antibodies which bind to SK007 cells can be used as positive controls for later screening procedures.

Hybridomas can then be screened for secretion of antibodies which do not react with basophil-bound IgE. A preferred method is to screen the antibodies for the inability to induce histamine release by basophils. The source of basophils for such histamine release assays is blood leukocytes from donors whose basophils are known to be very sensitive for induction of histamine release. An alternative and possibly less sensitive method is an immunofluorescence staining technique. Basophil leukocytes can be isolated from blood. Freshly isolated basophils have IgE on their surface. Monoclonal antibodies which do not bind basophil-bound IgE are specific for an epitope which is at or near a site occupied by the basophil FcεR (and hence is inaccessible for the monoclonal antibodies).

Hybridomas which produce parotope-specific anti-idiotypic antibody can be made by immunizing an animal with anti-IgE antibody and screening for antibodies which bind the parotope of the immunizing anti-IgE antibody. Immunization results in production of antibodies against the antigenic determinants on the anti-IgE antibody including the idiotype. Anti-idiotype antibodies are first screened for their binding to anti-IgE antibody and not other mouse antibodies. Those which are parotope-specific are screened on the basis of the antibody's ability to compete the binding of human IgE to the anti-IgE monoclonal antibody used for immunization.

Antibody fragments such as $F(ab')_2$, Fab and $F_V$ can be produced by standard techniques of enzyme digestion. In addition, synthetic peptides representing Fab and $F_V$ analogues can be produced by genetic engineering techniques. See e.g., Better, M. et al. (1988) *Science* 240:1041; Huston, J. S. et al., (1988) *Proc. Natl. Acad. Sci. USA* 85:5879–5883.

The chimeric anti-IgE antibodies are comprised of individual chimeric heavy and light immunoglobulin chains. The chimeric heavy chain is a contiguous polypeptide having a rodent (generally murine) heavy chain variable region or hypervariable regions and a human heavy chain constant region. The chimeric light chain is a contiguous polypeptide having a rodent light chain variable regions or hypervariable regions and human light chain constant region.

The chimeric antibodies can be monovalent, divalent or polyvalent. Monovalent antibodies are dimers (HL) formed of a chimeric heavy chain associated (through disulfide bridges) with a chimeric light chain. Divalent immunoglobulins are tetramers ($H_2L_2$) formed of two associated dimers. Polyvalent antibodies can be produced, for example, by employing heavy chain constant region which aggregate (e.g., mu type constant regions).

The variable regions of the chimeric antibodies are derived from the anti-IgE antibody of this invention. The heavy chain constant region can be selected from any of the five isotypes alpha, delta, epsilon, gamma or mu. Heavy chains of various subclasses (such as the IgG subclasses) can be used. The different classes and subclasses of heavy chains are responsible for different effector functions and thus, by choosing the desired heavy chain constant region, chimeric antibodies with desired effector function can be produced. The light chain constant region can be the kappa or lambda chain.

In general, the chimeric antibodies are produced by preparing a DNA construct which encodes each of the light and heavy chains components of the chimeric antibody. The construct comprises fused gene comprising a first DNA segment which encodes at least the functional portion of the murine variable region (e.g. functionally rearranged variable regions with joining segment) linked to a second DNA segment encoding at least a part of a human constant region. Each fused gene is assembled in or inserted into an expression vector. Recipient cells capable of expressing the gene products are then transfected with the genes. The transfected recipient cells are cultured and the expressed antibodies are recovered.

Genes encoding the variable region of rodent light and heavy chains can be obtained from the the hybridoma cells which produce the anti-IgE antibodies. For example, the murine hybridoma cell lines which produce murine anti-IgE antibody provide a source of variable region genes.

Constant regions genes can be obtained from human antibody producing cells by standard cloning techniques. Alternatively, because genes representing the two classes of light chains and the five classes of heavy chains have been cloned, constant regions of human origin are readily available from these clones.

Preferably, the fused genes encoding the light and heavy chimeric chains are assembled into expression vectors which can be used to cotransfect a recipient cell. Suitable vectors for the gene constructs include plasmids of the types pBR322, pEMBL and pUC. Each vector contains two selectable genes—one for selection in a bacterial system and one for selection in a eukaryotic system—each vector having a different pair of genes. These vectors allow production and amplification of the fused genes in bacterial systems and subsequent cotransfection of eukaryotic cells and selection of the cotransfected cells. Examples of selectable gene for the bacterial system are the genes which confer ampicillin and the gene which couples chloramphenicol resistance. Examples of selectable genes for eukaryotes are gpt and neo.

The preferred recipient cell line is a myeloma cell. Myeloma cells can synthesize, assemble and secrete immunoglobulins encoded by transfected antibody genes. Further, they possess the mechanism for glycosylation of the immunoglobulin. A particularly preferred recipient cell is the Ig-nonproducing myeloma cell SP2/0. Shulman et al, Nature 276:269 (1978). The cell produces only immunoglobulin encoded by the transfected immunoglobulin genes. Myeloma cells can be grown in culture or in the peritoneum of mice where secreted immunoglobulin can be obtained from ascites fluid. Other lymphoid cells such as B lymphocytes or hybridoma cells can serve as suitable recipient cells.

Lymphoid cells can be transfected with vectors containing immunoglobulin encoding genes in several ways. These include electroporation, protoplast fusion and calcium phosphate precipitation procedure. The resulting transfected cells provide continuous, stable cell lines which produce chimeric antibodies.

The chimeric antibodies can be produced in large quantity in large scale tissue culture systems such as various continuous perfusion systems, hollow fiber systems, static maintenance culture systems or other systems.

Near human antibodies or antibody fragments can also be produced by engineering gene sequences of human antibodies which encode the hypervariable (complementarity determining) regions to provide appropriate anti-IgE specificity. See e.g., Robert, S. et al., Nature 328:731-733 (1987); Better, M. et al., (1988) Science 240:1041.

The invention is illustrated further by the following exemplification:

EXEMPLIFICATION

Materials and Methods

Reagents

Three human IgE preparations were employed. Affinity purified polyclonal human IgE, that was subsequently absorbed over anti-human IgE, and anti-transferrin columns, were purchased from Ventrex (Portland, Me.). IgE myeloma PS was a kind gift from Dr. K. Ishizaka (The Johns Hopkins University, Baltimore, Md.). Fc fragments of IgEPS were prepared by papain digestion (Stanworth, D. R. and M. W. Turner. Immunochemical analysis of immunoglobulins and their subunits. In. Handbook of experimental immunology. ed. D. M. Weir, Vol. 1 Immunochemistry. Blackwell Scientific Publications. 1978. pg 6.16). Finally, IgE myeloma ND was isolated from culture supernatant of SKO-007 cells by affinity chromatography.

Affinity-purified human IgE, IgM, IgA and transferrin and the goat anti-mouse IgG (H+L, absorbed against human serum proteins) were purchased from Jackson Immunoresearch, Malvern, Pa. Purified reference monoclonal anti-human IgE Fc (HP6029 and HP6061), anti-human IgG Fc (HP6017) anti-human IgG Fd (HP6046), anti-human IgG4 Fc (HP6025), anti-human kappa (HP6062), anti-human lambda (HP6054) and anti-human IgM Fc (HP6081) were generated by the Hybridoma Reagent Laboratory, Houston, Tex. from clones produced by Dr. Charles Reimer (CDC, Atlanta, Ga.) (Reimer, C. B. et al. 1984. Evaluation of thirty-one mouse monoclonal antibodies to human IgG epitopes. Hybridoma 3:236). Streptavidin-horseradish peroxidase was purchased from KPL (Gaithersburg, Md.) while egg avidin and biotin-succinimide ester were obtained from Calbiochem Corporation (La Jolla, Calif.). RPMI 1640, and fetal bovine serum were purchased from GIBCO (Grand Island, N.Y.). All other chemicals, unless otherwise specified, were purchased from Sigma Chemical Co. (St. Louis, Mo.).

The cells used in binding experiments were obtained from the American Type Culture Collection: SKO-007 (human IgE-lambda ND-secreting myeloma, ATCC CRL 8033-2), IM-9 cells (human IgG secreting human lymphoblast, ATCC CCL 159), RPMI 8226 cells (human lambda-secreting myeloma, ATCC CCL 155), and RPMI 1788 cells (human IgM-secreting cell line, ATCC CCL 156).

Monoclonal anti-human IgE

BALB/c mice received three multisite subcutaneous injections with 50 μg of polyclonal human IgE in complete Freund's adjuvant, once each month for 3 months. Three days prior to fusion, mice were immunized intraperioneally with a final dose of 50 μg/ml of IgE in phosphate buffered saline (PBS; 0.14M NACl, 1.6 mM $KH_2PO_4$, 8.9 mM $Na_2HPO_4$, pH 7.4). On 4 separate occasions, spleen cells were fused with SP2/0 mouse myeloma cells (ratio 1/1) in polyethylene glycol 1500 (Kodak) using an established protocol. See International Patent Application No. PCT/US88/09181. Two weeks after fusion, hybridoma supernatants were collected and tested by enzyme immunoassay for their ability to bind human IgE ND and PS myelomas and not to other major human serum proteins (IgG, IgA, IgM, transferrin, serum albumin). Hybrids secreting antibody only reactive with human IgE were single cell cloned and expanded for ascites and large-scale supernatant production.

Selected monoclonal antibodies were purified from ascites or culture fluid by a dual column chromatography method. First, antibodies were chromatographed on DE-52 anion exchange resin (Whatman, Maidstone, England) using 0.05M Tris pH 8.0 with stepwise increments of NaCl from 0.01M to 0.15M. Antibody-containing fractions were identified by enzyme immunoassay, concentrated by Amicon filtration (Amicon, Danvers, Ma., YM10 membrane) and purified further on a hydroxylapatite column (Bio-Gel HT; BioRad, Richmond, Calif.) using a 0.01 to 0.3M phosphate buffer (pH 7.4) step gradient. Purity was assessed by isoelectric focusing (Hamilton, R. G., Reimer, C. B., Rodkey, L. S. 1987. Isoelectric focusing immunoblot analysis of mouse monoclonal antibodies to the four human IgG subclasses. Electrophoresis 8:127) and SDS-PAGE using the Pharmacia PHAST system (Pharmacia, Piscatway, N.J.) and the concentration determined by absorbance at 280 nm (1.5–1 mg/ml).

Purified monoclonal antibody was biotinylated by adding biotin-hydroxysuccinimide ester, dissolved at 10 mg/ml immediately prior to use in N,N-dimethylformamide (DMF), and added to the monoclonal antibody in PBS using a 8:1 molar ration of B-HSE:antibody. After overnight rotation at 4° C., the preparation was dialyzed 24 hr against PBS (10,000 MW cutoff). Cyrstalltne BSA was added to 10 mg/ml and the conjugate was tested for immunoreactivity to human IgE by EIA.

Immunochemical Characterization of Monoclonal Antibodies

Specificity of the antibodies was determined by solid phase enzyme immunoassay (EIA). Purified human proteins (polyclonal IgE, IgE ND and IgE PS myeloma proteins, IgEFc-PS, IgG, IgM, IgA, transferrin, serum albumin) were diluted in PBS to 1 or 10 $\mu$g/ml and coated at 0.1 ml/well onto Immunolon II removawells (Dynatech, McClean Va.) overnight at 4° C. Unreacted sites were blocked with PBS-1% BSA (PBS-B, 0.2 ml/well) for 1 hr at room temperature. All wells were washed 3 times with PBS-0.05% Tween 20 (PBST). Test and control MAbs in ascites or chromatographically purified form were then added to their respective wells (0.1 ml/well, ascites at $\geq$1:1000 dilution; purified antibody at 10 ng/ml-1 $\mu$g/ml in PBS-B). After 2 hrs at 37° C., the plates were washed with PBST and 100 $\mu$l of a 1:3000 dilution of horseradish peroxidase-conjugated goat anti-mouse IgG(H+L), preadsorbed against human serum proteins, was added to each well. Following 1–2 hrs at 37° C., plates were again washed with PBST and 100 $\mu$l of TMB substrate was added: 200 $\mu$l of 1% 3,3'5,5' tetramethylbenzidine (T-2885, Sigma) in DMF, 27 $\mu$l 3% $H_2O_2$ in 20 ml of 0.02M acetic buffer, pH 6.0. The blue product was converted to yellow and the reaction was stopped with 4N $H_2SO_4$ (50 $\mu$l/well). Optical density (OD) was read at 450 nm (BioTek, Winooski, Vt.). Net OD was computed by subtracting buffer blank ODs and the mean of replicate net OD measurements of antibody binding to insolubiltzed human IgE was compared to binding to wells coated with human IgG and other human serum proteins.

The class and subclass of the murine antibodies were determined by EIA using a format similar to that described above the the exception of alkaline phosphatase-conjugated polyclonal goat anti-mouse IgG1, IgG2a, IgG2b, IgG3, kappa or IgM detection antibodies from Souther Biotechnology, Birmingham, Ala. and p-nitrophenylphosphate as substrate. All murine IgG monoclonal antibody subclasses were confirmed by immunodiffusion using a 1% agarose gel (SeaKem MC agarose, FMC, Rockland, Me.) in PBS and polyclonal rabbit anti-mouse IgG1, IgG2a, IgG2b and IgG3 antisera from Litton Bionetics, Kensington, Md.

The ability of selected monoclonal antibodies to bind to similar regions of the IgE molecule was examined by a competitive inhibition EIA using a checkerboard analysis. A limiting amount of human IgE (Ventrex, polyclonal) was coated on microtiter plate wells (0.8 $\mu$g/ml of PBS, 0.1 ml/well, overnight, 4 C). Without washing, the wells were then blocked with PBS-B (0.2 ml/well, 2 hr at RT). The wells were washed three times with PBS-T and 0.1 ml of unlabeled monoclonal antibody (20 $\mu$g/ml to 2 ng/ml in PBS-BSA) were pipetted into their respective wells and incubated overnight at 4 C. Without washing, 0.05 ml of a biotinylated MAb was added to all wells in the plate and allowed to react for 1 hr at RT. The plates were washed and streptavidin-HRP was added to all wells (0.1 ml, 1:8000 dilution in PBS-BSAd). After 1 hr at RT, the plate was washed with PBS-T and developed with TMB as discussed above. The optimal concentration of biotin-monoclonal antibody was determined in a previous experiment to insure good immunoreactivity and the addition of limiting amounts of labeled monoclonal antibody. In previous experiments, a sequential method of labeled and unlabeled monoclonal antibody addition was shown to generate, sharper, more definitive inhibition results than the simultaneous addition competition binding EIA. For this reason, all competitive inhibition assays were performed with sequential reagent addition. Inhibition assays were performed using 6–12 dilutions of unlabeled monoclonal antibody to obtain inhibition curves. Results from these assays are presented as a percent of the homologous monoclonal antibody inhibition using interpolation from the homologous monoclonal antibody inhibition curve.

The affinities of the non-histamine releasing antibodies and randomly selected monoclonal antibodies that induce release for human IgE were determined using minor modifications of a previously reported non-competitive solid phase immunoassay method (Beattry J. D., Beatty B. G., Vlahos W. G. 1987. Measurement of monoclonal antibodies by non-competitive enzyme immunoassay. J. Immunol. Methods 100:173–179). The assay employs serial dilutions of both antigen (IgE) coated on the plate and purified monoclonal antibody. Each row of a microtiter plate was coated with decreasing 2 fold concentrations of polyclonal IgE starting at 0.2 $\mu$g/ml in PBS (0.1 ml/well, overnight, 4 C). All wells were blocked with PBS-B (200 $\mu$l, 2 hr, 23 C), the plate washed and serial dilutions (6 or 12) of a single MAb were incubated in each row (0.1 ml/well, 2 hr, 23C0. The plate was rewashed and bound monoclonal antibody was detected as discussed in the screening EIA. The affinity constant was computed using the formula: $\frac{1}{2}(2[AB']-[AB])$, where Ab is the monoclonal antibody concentration in the well that produces 50% of the maximum OD obtained in the row coated with the first amount of IgE. AB' is the MAb concentration that produced a 50% maximum OD in the row coated with $\frac{1}{2}$ the amount of IgE.

Human Basophil Studies

The ability of the monoclonal antibodies to bind onto and induce histamine release from peripheral blood basophils was assessed using cells from extensively-studied atopic patients and healthy volunteers at the Johns Hopkins University School of Medicine. In these studies, basophils were partially purified from the blood of atopic individuals using elutriation and density gradient centrifugation (Warner J. A., Reshef A., Macglashan D. W. Jr.: A rapid percoil technique for the purification of human basophils. J. Immunol. Methods 105:107–110, 1987). In the first set of experiments, the 42 test anti-human IgE MAbs in ascites and 3 purified control monoclonal antibodies (see table 3) were incubated at 3 or more dilutions (1:100, 1:1000, 1:10,000) with basophil preparations from at least 3 donors. Histamine was measured in the cell supernatants using a fluorometric assay (Siraganian R. P. 1975. Refinement in the automated fluorometric histamine analysis system. J. Immunol. Meth. 30:1). Each antibody that reproducibily demonstrated no ability to release histamine was retested using basophils isolated from the blood of at least 2 patients whose basophils released well to low levels of polyclonal anti-human IgE (defined as super releasers) (Lichtenstein L. M., and MacGlashan D. W. Jr.: 1986. The concept of basophil relasibility. J. Allergy Clin. Immunol. 77:291-294). All basophil histamine release results were compared to total basophil histamine content as determined by cell lysis. All basophil preparations were controlled using a polyclonal anti-human IgE control that triggered the release of >50% of the total cell histamine content.

B-Cell Binding Assays

Human SKO-007, CCL-156 and CCL-159 mcells, containing surface-bound human IgE-lambda, IgM-lambda and IgG1-kappa, respectively, were maintained in RPMI medium 1640 supplemented with 5% fetal bovine serum and 2 mM glutamine from GIBCO and 1% antibiotic-antimycotic solution. Peripheral blood mononuclear cells obtained by venipuncture of healthy donors were prepared by Ficoll-paque (Pharmacia, Piscataway, N.J.) density gradient centrifugation. Binding of MAbs to cell surfaces was assessed using two types of assays: binding of antibodies to live cells followed by indirect fluorescent flow cytometric analysis and an enzyme-linked antibody assay with the cells attached to microtiter plates.

Binding of monoclonal antibodies to live cells was performed by pelleting the cells by centrifugation at $300 \times g$ for 5 min, washing maintenance media from the cells with PBS-BSA and resuspending the cells at $20 \times 10^6$ in PBS-B. Fifty $\mu l$ of cell suspension was mixed with 50 $\mu l$ of monoclonal antibody at twice the stated concentrations (1–10 $\mu g/ml$) in PBS-B and kept on ice. After a 30 min incubation, 2 ml of ice cold PBS-B was added to each tube, and the cells were collected by centrifugation at $300 \times g$ for 5 min at 5° C. Supernatant was decanted, cell pellets resuspended by vortexing and cells washed once with an additional 2 ml of PBS-B. After collecting the cells by centrifugation, 20 $\mu l$ of affinity purified goat F(ab')$_2$ anti-mouse IgG (H+L) (Boehringer Mannhelm, Lot 52934, code 60529) diluted 1:20 in PBS-B was added to each tube. The tubes were incubated 20 min on ice and washed with PBS-B as above. Finally, cell pellets were resuspended in 0.5 ml of 1% paraformaldehyde (Polysciences Inc., Warrington, Pa.) in PBS. Cells were analyzed using a EPICS Profile (Coulter) equipped with a 5 W argon laser running at 488 nm, 0.6 W at Cytology Technology, Inc. (Houston, Tex.). Fluorescence intensity was collected with a built-in logarithmic amplifier after gating on the combination of forward light scatter and perpendicular light scatter to discriminate viable cells.

The cell-bound enzyme-linked antibody assay was performed by binding MAbs to glutaraldehyde-fixed cells according to the method of Kennett, R. H. in "Enzyme-linked Antibody Assay With Cells Attached To Polyvinyl Chloride Plates" in *Monoclonal Antibodies Hybridomas: A New Dimension in Biological Analyses*, ed. Kennett et al., 1980, pg. 376. Poly-1-lysine (100 $\mu l$/well, 10 $\mu g/ml$ in PBS) was added to flat bottomed microtiter plates (Falcon #3072, Becton Dickinson Labware, Oxnard, Calif.). This solution was flicked out of the wells after 30 min at 22° C. and 50 $\mu l$ of cells at $2.5 \times 10^6$ cells/ml of calcium and magnesium-free Dulbecco-modified PBS (GIBCO) was added to each well. Cells were deposited on the bootom of the wells by centrifugation at $300 \times g$ for 5 min and cells were fixed at 22° C. for 10 min by adding 50 $\mu l$ of glutaraldehyde diluted to 0.25% in ice-cold PBS. Non-specific binding sites were blocked by sequential incubation of 0.1M glycine-0.1% BSA in PBS (200 $\mu l$/well) followed by Blotto [5% non-fat dry milk (Carnation, LA, Calif.) in PBS with 1 g/L of thimerosal]. Blocking solutions were removed by gentle flicking of the plate. Cells were exposed to 50 $\mu l$/well of control or rest monoclonal antibody in Blotto for 1 hr at 37° C. Unbound antibody was removed by flicking the plate and washing 6 times with 200 $\mu l$/well of PBS using a Transtar 96 pipetting device (Costar, Cambridge, Mass.). Subsequently, the cells were incubated with 50 $\mu l$ biotin-labeled affinity-purified goat anti-mouse IgG (KPL, Gaithersburg, Md.) at 0.5 $\mu g/ml$ in Blotto for 1 hr at 37° C. All wells were washed as above and horseradish peroxidase-streptavidin was added at 0.5 $\mu g/ml$ in Blotto for 1 hr at 37° C. Unbound conjugate was removed by washing as above and 100 $\mu l$ of TMB substrate was added. The plates were kept in the dark for 30 min at 22° C. and the reaction was stopped with the addition of 50 $\mu l$/well of 4N $H_2SO_4$. Optical density at 450 nm was measured using a Biotek microtiter plate reader.

RESULTS

Specificity for Human IgE

Due to possible allotypic and functional variation among human IgE myeloma proteins an affinity-purified polyclonal IgE from multiple human donors was used as the immunogen and specific monoclonal antibody was screened using purified human IgE myeloma proteins as well as polyclonal IgE. Hybridomas secreting IgE-specific monoclonal antibody were selected from four separate fusions based on the initial criterion of strong reactivity to IgE ND, IgE PS and polyclonal IgE and not to human IgG, IgM, IgA, transferrin and serum albumin. Several hundred. positive clones were produced that met this criterion and 41 were selected for expansion and ascites production in pristane-primed mice because of their exceptionally strong reactivity to IgE at high culture fluid dilutions. They showed no detectable reactivity (<0.01% crossreactivity) to chromatographically purified human IgG, IgM, IgA, transferrin, and serum albumin in repeated immunoassay analyses.

Human Basophil Histamine Release

The 41 selected monoclonal antibodies were further subdivided according to their ability to induce histamine release from IgE-bearing human basophils. Due to the concern about variable releasability of mediators from basophils of different donors, all monoclonal antibodies were screened at by DM using 3 to 6 dilutions of ascites and partially purified basophil preparations from at least 4 donors. This initial screening identified 29 of the 41 monoclonal antibody as effective inducers of histamine release (Table 1). Control monoclonal anti-IgG (HP6017), HP6046), anti-IgG4 (HP6025), anti-IgM (HP6081) monoclonal antibody did not induce histamine release, even with the basophils obtained from several atopic patients that had been previously classified at sensitive histamine releasers. The remaining 12 anti-human IgE monoclonal antibodies that did not induce histamine release (Table 2) were then subjected to a subsequent immunochemical and cell binding analyses.

parable affinity constants were obtained when PS IgE myeloma protein was used as the antigen. All 12 monoclonal antibodies bound equally well to the Fc fragment and intact molecule of IgE PS with two exceptions.

TABLE 1

MONOCLONAL ANTI-HUMAN IgE CHARACTERIZATION
(Histamine Releasers)

| Clone Number | Specificity IgE:IgEFc % | Basophil HR %* .1k | 1k | 10k | FCA IgE B-Cell Binding % | IgG Subclass |
|---|---|---|---|---|---|---|
| E10.74.28 | 100:<.01 | 60 | 65 | 3 | 20 | 1-k |
| E688.13 | 100:0.3 | 86 | 91 | 90 | 18 | 1-k |
| E608.10 | 100:1 | 81 | 84 | 86 | 23 | 1-k |
| E10.33.22 | 100:7 | 77 | 74 | 16 | 15 | 2a-k |
| E10.100.9 | 100:20 | 68 | 45 | 0 | 34 | 2a-k |
| E10.68.10 | 100:24 | 56 | 42 | 2 | 23 | 1-k |
| E10.95.3 | 100:28 | 65 | 68 | 3 | 52 | 2b-k |
| E10.80.4 | 100:30 | 85 | 92 | 90 | 22 | 2b-k |
| E10.5.83 | 100:50 | 82 | 80 | 6 | 17 | 1-k |
| E10.10.3 | 100:51 | 85 | 78 | 2 | 24 | 1-k |
| E10.41.16 | 100:62 | 95 | 91 | 91 | 52 | 2a |
| E10.27.5 | 100:63 | 68 | 90 | 9 | 32 | 2b-k |
| E10.24.28 | 100:69 | 79 | 89 | 5 | 29 | 2b-k |
| E10.3.14.25 | 100:80 | 68 | 58 | 3 | 23 | 1-k |
| E10.1.88 | 100:93 | 72 | 55 | 2 | 21 | 1-k |
| E10.61.6 | 100:93 | 81 | 78 | 70 | 14 | 1-k |
| E10.40.62 | 100:95 | 37 | 24 | 9 | 72 | 2b-k |
| E10.22.84 | 100:95 | 77 | 84 | 15 | 44 | 2a-k |
| E545.4 | 100:95 | 24 | 3 | 0 | 15 | 1-k |
| E10.14.52 | 100:95 | 52 | 24 | 0 | 20 | 1-k |
| E10.71.47 | 100:95 | 30 | 16 | 0 | 18 | 1-k |
| E235.6 | 100:96 | 52 | 25 | 12 | 27 | 1-k |
| E10.18.3 | 100:98 | 33 | 26 | 0 | 13 | 1-k |
| E69-2 | 100:99 | 22 | 32 | 43 | 57 | 1-k |
| E10.19.12 | 100:99 | 28 | 37 | 36 | 52 | 1-k |
| E10.52.38 | 100:99 | 52 | 64 | 12 | 22 | 1-k |
| E10.25.44 | 100:99 | 31 | 26 | 0 | 23 | 2b-k |
| E10.54.26 | 100:99 | 34 | 17 | 2 | 17 | 1-k |
| E10.7.19 | 100:99 | 38 | 26 | 6 | 28 | 1-k |
| Controls | | | | | | |
| HP6017 | 0:0 | 100(GFc) 0 | 0 | 0 | 0  40(G) | 2a-k |
| HP6046 | 0:0 | 100(GFd) 0 | 0 | 0 | 0 | 1-k |
| HP6025 | 0:0 | 100(G4Fc) 0 | 0 | 0 | 0 | 1-k |
| HP6081 | 0:0 | 100(M) 0 | 0 | 0 | 0  60(M) | 1-k |
| HP6029 | 100:99 | 40 | 52 | 20 | 45 | 1-k |

*The basophil histamine release studies were performed with these MAb in ascites at dilutions of 100 (0.1K), 1000 (1K) and 10,000 (10K).
**The fluorescent cytometric assay (FCA) results are presented as the % of cells that fell above a 5% threshold window set using SKO-007 cells incubated only with only FITC-labeled secondary antibody.

The 12 non-releasing monoclonal antibodies were first chromatographically purified using ion exchange chromatography. Their purity and concentration were determined and their immunoreactivity for human IgE was reconfirmed. Their affinities for polyclonal human IgE ranged from 0.2 to $30.1 \times 10^8$ L/M (Table 1). Com- E8.13.1 demonstrated a preference for the IgE Fc fragment while E10.55.31 bound preferentially to the Fab of IgE. The 29 histamine releasing antibodies demonstrated a broad spectrum of relative reactivity between IgE Fc and intact IgE (Table 2).

TABLE 2

MONOCLONAL ANTI-HUMAN IgE CHARACTERIZATION
(Non-Histamine Releasers)

| Clone | Specificity IgE:IgEFc % | Basophil HR % | FCA IgE-B Cell % | EIA IgE-B Cell | Affinity Constant ($10^8$ L/M) | IgG Subclass | pI Range |
|---|---|---|---|---|---|---|---|
| E11.4.70 | 100:90 | 0 | 45 | + | 30.1 | 2b-k | 7.1–7.4 |
| E10.8.120 | 100:98 | 0 | 35 | + | 3.2 | 1-k | 6.7–7.2 |
| E101.1 | 100:98 | 0 | 14 | + | 2.7 | 2a-k | 7.2–7.8 |
| E10.21.15 | 100:99 | 0 | 14 | + | 2.5 | 1-k | 5.6–6.2 |
| E10.12.55 | 100:98 | 0 | 14 | − | 4.0 | 2a-k | 6.6–7.5 |
| E357.4 | 100:95 | 0 | 0 | − | 3.8 | 1-k | 7.3–7.6 |
| E8.5.3 | 100:94 | 0 | 8 | − | 3.3 | 2b-k | 6.1–6.8 |
| E8.32.9 | 100:93 | 0 | 4 | − | 3.4 | 1-k | 5.6–6.0 |
| E8.4.17 | 100:93 | 0 | 0 | − | 1.6 | 2b-k | 5.7–6.1 |
| E8.37.4 | 100:90 | 0 | 3 | − | 0.9 | 1-k | 5.6–6.1 |
| E8.13.1 | 40:100 | 0 | 8 | − | 0.2 | 1-k | 7.0–7.6 |

TABLE 2-continued

MONOCLONAL ANTI-HUMAN IgE CHARACTERIZATION
(Non-Histamine Releasers)

| Clone | Specificity IgE:IgEFc % | Basophil HR % | FCA IgE-B Cell % | EIA IgE-B Cell | Affinity Constant ($10^8$ L/M) | IgG Subclass | pI Range |
|---|---|---|---|---|---|---|---|
| E10.55.31 | 100:0.3 | 0 | 5 | — | 0.5 | 1-k | 7.1–7.6 |

*All MAbs in this table demonstrated <0.01% binding to human IgG, IgA, IgM, transferrin and serum albumin.
*Binding of <10% to IgE-surface bearing cells (SKO-007) in the cell binding studies was considered a conservative criterion for negative binding. Results from the FACS cell binding assay are reported using purified MAb at 10 ug/ml with the exception of E8.13.1, E10.55.31, E8.37.4 and E357.4 which were tested at a 1:200 dilution of ascites.
All MAb in this table demonstrated <1% binding to non-IgE-surface bearing control cells (RPMI-1788, IM9 and PBL) in the FCA and cell binding EIA.

The non-histamine releasing property of the twelve monoclonal antibodies selected by the first cycle of testing were verified by DM in a second set of experiments using basophils isolated from the blood of super-releaser donors. Additionally, the inability of these monoclonal antibodies to release histamine from sensitized human basophils was independently confirmed by Dr. Reuben Siriganian at the NIH. The reactivity of these monoclonal antibodies for IgE was repetitively quality controlled by immunoassay throughout the course of these expermients.

The possibility that these antibodies might bind to IgE on the basophil but not be capable of cross-link IgE due to affinity or steric constrains through the use of anti-mouse IgG enhancement was also explored. A polyclonal goat antibody specific for mouse IgG and preabsorbed against human immunoglobulins was selected as a second antibody to enhance cross-linking of any mouse antibody that was bound to IgE-bearing basophils. In the absence of any other reagent except sensitized basophils, this anti-mouse IgG alone did not incude histamine release. When added at an appropriate concentration to basophils that had been preincubated with a varying amounts of a positive control, histamine releasing monoclonal antibody (E10.100.9), an enhancement of histamine release was observed as evidenced by a shifting of the histamine-release curve. None of the twelve HR positive monoclonal antibodies demonstrated any ability to induce the release histamine from IgE-bearing basophils, even in the presence of a wide range of anti-mouse IgG concentrations. These monoclonal antibodies not only do not induce histamine release but they also do not bind onto the surface of IgE-bearing basophils.

IgE-secreting B-cell Binding

The well-characterized SKO-007 subclone of US66 was selected as an IgE-secreting B-cell for testing the binding capability of the entire panel of human IgE-specific monoclonal antibodies. The rate of IgE secretion (1–10 μg/ml) of the SKO-007 cells maintained in culture was comparable to that reported by others. All of the histamine releasing antibodies bound effectively to live and fixed SKO-007 cells. Only four of the 12 non-histamine releasing monoclonal antibodies (E11-4-70, E10.8-120, E101.1 and E10-21-15) bound reproducibly to IgE attached to the surface of SKO-007 cells in both the fluorescent cell binding assay and the cell binding EIA (Table 1). Antibodies E357-4, E32-9, E8-4-17, E8-37-4, and E10-55-31 did not bind to SKO-007 cells. Comparable patterns of reactivity were observed in the enzyme-linked cell assay. To control for the binding of these monoclonal antibodies to other cell surface molecules, they were incubated with IgM and IgG bearing B-cell lines (RPMI 1788 and IM9). None of the 41 anti-human IgE monoclonal antibodies reacted detectably to these two control cells lines or isolated human peripheral blood leukocytes from a healthy donor in either the fluorescent cytometric assay or the cell-based EIA. The hybridoma cell line producing the monoclonal antibody E357-4 was deposited at the American Type Culture Collection, 12301 Parklawn Drive, Rockville, Md. 20852, on Oct. 26, 1991, and was assigned accession number HB 10906.

Equivalents

Those skilled in the art will recognize or be able to ascertain using no more than routine experimentation, many equivalents to the specific embodiments of the invention described herein. Such equivalents are intended to be encompassed by the following claims.

I claim:

1. An antibody which binds to soluble IgE but does not bind to IgE on IgE-expressing B-cells or to IgE bound to basophils and which does not induce histamine release by mast cells or basophils.

2. An antibody of claim 1, which is monoclonal.

3. An antibody of claim 2, which is a chimeric murine/human antibody having an antigen binding region of murine origin and a constant region of human origin.

4. An antigen-binding fragment of the antibody of claim 1.

5. An antigen-binding fragment of claim 4, selected from the group consisting of $F_V$, Fab, Fab', and F(ab)'$_2$.

* * * * *